United States Patent [19]

van der Burg

[11] 4,125,718
[45] Nov. 14, 1978

[54] AMINO-SUBSTITUTED TETRACYCLIC COMPOUNDS

[75] Inventor: Willem J. van der Burg, Heesch, Netherlands

[73] Assignee: Akzona Incorporated, Asheville, N.C.

[21] Appl. No.: 851,770

[22] Filed: Nov. 15, 1977

Related U.S. Application Data

[60] Continuation of Ser. No. 651,759, Jan. 23, 1976, abandoned, which is a division of Ser. No. 463,636, Apr. 24, 1974, Pat. No. 3,950,425.

[30] Foreign Application Priority Data

May 2, 1973 [NL] Netherlands .................. 7306069

[51] Int. Cl.² .................. C07D 413/06; C07D 313/10
[52] U.S. Cl. .................................. 544/145; 544/147; 260/327 B; 260/333
[58] Field of Search ............... 544/145, 147; 260/333, 260/327 B

[56] References Cited

PUBLICATIONS

Akzo, "Chem. Abstracts", vol. 82 (1975) No. 170,732a.

Primary Examiner—Henry R. Jiles
Assistant Examiner—R. W. Ramsuer
Attorney, Agent, or Firm—Robert H. Falk; Charles A. Wendel; Francis W. Young

[57] ABSTRACT

The invention discloses novel compounds of the general formula:

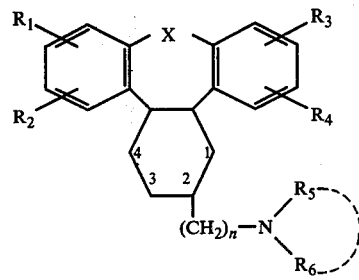

and salts thereof, in which
X stands for oxygen, sulphur, the group >$NR_7$ or the group —$CR_8R_9$—;
$R_1$, $R_2$, $R_3$ and $R_4$ represent hydrogen, hydroxy, halogen, alkyl (1-6 C), alkoxy (1-6 C), alkylthio (1-6 C) or trifluoromethyl;
$R_5$ and $R_6$ represent hydrogen, alkyl (1-6 C), aralkyl (7-10 C) or together in combination with the nitrogen atom a heterocyclic five- or six-membered ring;
$R_7$ stands for hydrogen or alkyl (1-4 C);
$R_8$ and $R_9$ stand for hydrogen or methyl,
n is the number 0, 1 or 2 and
the dotted line means an optional C—C bond, with valuable central nervous system (CNS) activities, especially antidepressant activity.

27 Claims, No Drawings

AMINO-SUBSTITUTED TETRACYCLIC COMPOUNDS

CROSS-REFERENCE TO RELATED APPLICATION

This is a continuation of application Ser. No. 651,759 filed Jan. 23, 1976, now abandoned which in turn is a division of Ser. No. 463,636 filed Apr. 24, 1974, now U.S. Pat. No. 3,950,425.

The present invention relates to novel biologically active amino-substituted tetracyclic compounds and to processes for the preparation thereof.

It was found that compounds of the general formula I:

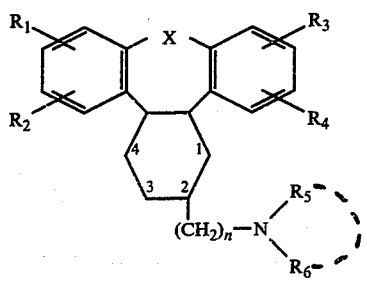

as well as the pharmaceutically acceptable salts thereof, in which
X stands for oxygen, sulfur, the group >$NR_7$ or the group —$CR_8R_9$—;
$R_1$, $R_2$, $R_3$ and $R_4$ represent hydrogen, hydroxy, halogen, alkyl (1–6 C), alkoxy (1–6 C), alkylthic (1–6 C) or trifluoromethyl;
$R_5$ and $R_6$ represent hydrogen, alkyl (1–6 C), aralkyl (7–10 C) or together in combination with the nitrogen atom a heterocyclic five- or six-membered ring;
$R_7$ stands for hydrogen or alkyl (1–4 C);
$R_8$ and $R_9$ stand for hydrogen or methyl,
$n$ is the number 0, 1 or 2 and
the dotted line means an optional C-C bond,
possess valuable C.N.S. activities. The toxicity of these compounds is exceedingly low.

The compounds according to the invention may be prepared in a manner commonly used for analogous compounds.

A very easy starting point for the synthesis of the compounds in question is a compound of the general formula II:

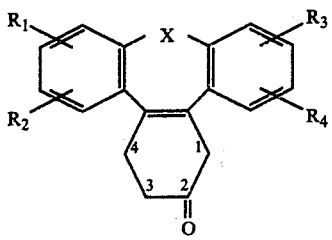

in which $R_1$, $R_2$, $R_3$, $R_4$ $R_4$ and X have the meanings mentioned above. The compounds II are, as far as known, novel compounds.

The starting material II can be prepared in various manners. The most simple method to prepare the compound II is the condensation of vinylmethylketone

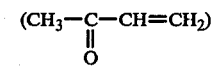

with a compound of the general formula III:

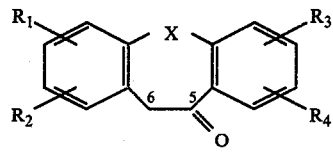

in which $R_1$, $R_2$, $R_3$, $R_4$ and X have the meanings mentioned above. This condensation reaction in preparing the starting material II is performed in a suitable solvent, preferably in the presence of a base, such as sodium hydroxide, potassium hydroxide, sodium ethoxide or sodium hydride. An intermediate product formed in this condensation reaction, namely a compound of formula III with γ-keto-butyl moiety at position 6, can, if desired, be isolated though it is not necessary to do so.

Starting from a compound with formula II the end-products according to formula I can be prepared in various manners. All these routes are known per se and are standard procedures commonly used for the preparation of similar compounds.

The method, which can generally be used in preparing the compounds I of the invention, consists of the condensation of a compound with the general formula IV:

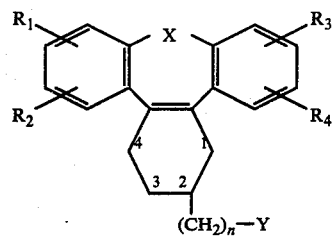

in which $R_1$, $R_2$, $R_3$, $R_4$, $n$ and X have the meanings specified before and Y represents a suitable leaving group, such as halogen or an etherified or esterified hydroxyl group, with ammonia or an amine according to the general formula V:

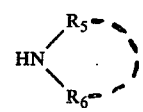

or an acid addition salt thereof, in which $R_5$ and $R_6$ have the meanings defined previously.

Leaving groups are well defined groups, described in various chemical handbooks.

Suitable leaving groups for this condensation reaction are for example a tosyloxy group, a mesyloxy group, a p-bromophenyl-sulphonyloxy group, a chlorine, bromine or iodine atom.

The compound IV required for this condensation reaction may be prepared from the starting material II described before by reducing the keto group to a hydroxy group, preferably with metal hydrides such as $LiAlH_4$, diboran or in particular $NaBH_4$, followed by converting this hydroxyl group into the desired leaving group in a conventional manner, for instance by tosylation, mesylation, reaction with SOCl$_2$, PCl$_5$, PBr$_3$, etc.

Extension of the alkyl chain (from $n=0$ to $72=1$ or can be performed in the usual way, for instance by treating a compound IV, in which $n=0$, with a cyanide such as potassium- or sodiumcyanide. The cyanogroup in the compound thus obtained can either be reduced to the corresponding aminomethylgroup or be hydrolysed to the corresponding carboxyl group. The aminomethyl compound is then treated with nitrous acid at low temperature (Piria), whereas the carboxyl compound is reduced. Both reactions afford the hydroxy-methyl compound. Finally the hydroxy-methyl compound thus obtained is converted into a compound in which the hydroxyl group is replaced by a leaving group.

By repeating the above-mentioned reaction steps, a further extension of the alkyl chain is obtained.

The primary amines according to the general formula I can further be prepared by reduction of the cyanide or azide group of compounds with the general formula VI:

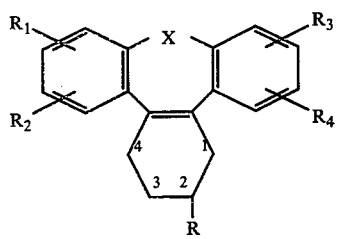

VI in which R represents one of the following moieties: —(CH$_2$)$_{n-1}$—CN or —(CH$_2$)$_n$—N$_3$, and in which R$_1$, R$_2$, R$_3$, R$_4$, X and $n$ have the meanings indicated before. These primary amines can additionally be converted in a conventional manner into the corresponding secundary or tertiary amines I.

The reduction is performed in the usual way for this kind of compounds. The cyanide group is preferably reduced by means of methalhydrides, especially lithium-aluminium-hydride, the azide group by a metalhydride such as LiAlH$_4$ or NaBH$_4$ or by hydrogenation in the presence of a metal catalyst such as palladium, Raney nickel, etc.

The starting materials with formula VI required in this method can, for example, be prepared by treating a compound of formula IV with sodium or sodium azide.

A simple and direct method in preparing a compound I (with $n = 0$) consists of the reaction of the starting material II with the amine according to formula V in the presence of a reducing agent. Suitable reducing agents in this connection are metalhydrides, e.g. NaBH$_4$, LiAlH$_4$, NaCNBH$_3$, etc., but preferably formic acid (Leuckart reaction) or hydrogen in the presence of a suitable catalyst, such as palladium, palladium on charcoal, Raney nickel, etc.

This reductive amination is well-known in organic chemistry and described in any chemical handbook.

The primary amines of the invention (with $n = 0$) can further be prepared by reduction of the oxime moiety of a compound of the general formula VII:

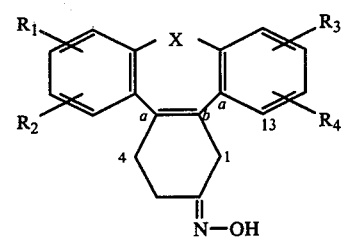

VII in which R$_1$, R$_2$, R$_3$, R$_4$ and X have the meanings indicated before.

This reduction may be performed by hydrogenation preferably in the presence of a metal catalyst, or with metal-hydrides such as LiAlH$_4$.

The compound VII is prepared direct from the corresponding keto compound II by treating the latter with hydroxylamine in the usual way, or indirect from the keto compound II by reacting it with isoamylnitrite/potassium-t.butoxide yielding the 2-keto-3-oxime compound, followed by a Wolff-Kishner reduction of the keto group.

A very convenient method for the preparation of the compounds I with $n \geq 1$ is the reduction of an amide of the general formula VIII:

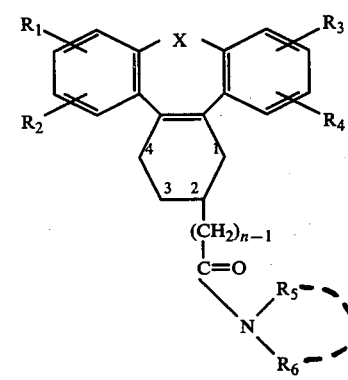

VIII in which R$_1$, R$_2$, R$_3$, R$_4$, R$_5$, R$_6$, X and $n$ have the meanings defined previously.

The reduction is carried out in a conventional manner for the reduction of amides, for example with metalhydrides, especially LiAlH$_4$.

The starting compounds VIII for this reduction can, for example, be prepared by hydrolysis of the cyano-compound of the general formula VI, yielding the corresponding carboxyl compound, which compound is converted into the corresponding amide in the usual way, for example by halogenating the carboxyl group affording the acid halide, followed by reacting the acid halide with an amine of the formula V. The primary amide of formula VIII may, of course, be prepared directly by partial hydrolysis of the cyano-compound VI.

Finally the present compounds of the invention with general formula I may be prepared by a reduction of the double bond $\Delta^{1(2)}$ of a compound with the general formula IX:

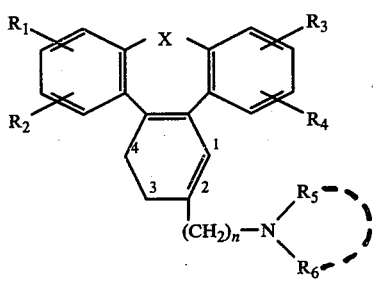

IX in which $R_1$, $R_2$, $R_3$, $R_4$, $R_5$, $R_6$, X and $n$ have the meanings mentioned previously.

This reduction is carried out in a conventional manner, for example with metalhydrides, such as LiAlH$_4$, etc. or by hydrogenation in the presence of a catalyst such as palladium, palladium on charcoal, Raney nickel etc.

The starting compounds IX may be prepared in various manners. For example, a compound IX with $n = 0$ (enamine) may be prepared by treating the ketone II with an amine of formula V, preferably in the presence of a Lewis acid, such as AlCl$_3$, SnCl$_4$, etc.

A compound IX with $n = 1$ may be prepared by treating the ketone II with HCN, eliminating the hydroxyl group formed to obtain a double bond and converting the cyano group in a conventional manner into an aminomethyl group. Another method consists of the reaction of the ketone II with the reagent (CH$_3$)$_2$S($\rightarrow$O)=CH$_2$, whereupon the compound thus obtained is treated with the amine V followed by eliminating the hydroxyl group formed to obtain a double bond.

A compound IX with $n = 2$ may be obtained by a Wittig reaction, a Wittig-Horner reaction, a Reformatski reaction or a reaction with acetonitril caried out on the starting ketone II. Reagents necessary in these reactions are well-known and described in any chemical handbook, for example: Ph$_3$P'CH—B (Wittig), (EtO)$_2$—P($\rightarrow$O)—CH$_2$—COR' in NaH and a suitable solvent (Wittig-Horner), BrZn—CH$_2$—COR' (Reformatski) and CH$_3$CN in the presence of sodiumalkoxide, whereby Ph stands for an aryl group, in particular a phenyl group, B represents a

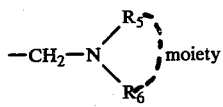

or a group that can easily be converted into this aminomethyl moiety, such as a carboxyl group, an esterified carboxyl group, an amide group, a cyano group or a hydroxyl group, and R' stands for an esterified hydroxyl group.

The Reformatski reaction requires an additional step to obtain the $\Delta 1(2)$ double bond by eliminating the hydroxy group formed, whereas in all methods in which the amino-moiety is not present already in the reagent used, an additional reaction has to be carried out in order to convert the moiety present (carboxyl, hydroxy, cyano, amide, etc.) into the desired amino-moiety.

Most reactions described preparing the starting material IX involve the reduction of a cyano group or an amide group. It is, of course, possible to reduce these moieties simultaneously with the Al(2) double bond present in the molecule.

In all afore-mentioned methods, in which a reduction has been carried out in the last step of the synthesis or in one or the previous steps, the conjugated double bond between the phenyl nuclei is not reduced under the usual reaction conditions.

By carrying out the reduction in question under strong reductive conditions, e.g. by increasing the reaction temperature and reaction time, by increasing the quantity of the reducing agent and/or performing the reduction under high pressure, it is possible to isolate also the compounds I with a saturated C—C bond instead of the C=C bond in particular where a catalytic hydrogenation with PtO$_2$ in acetic acid has been used for the reduction.

A more preferred synthesis for the preparation of these "saturated" compounds I consists of the reduction of the compound VII:

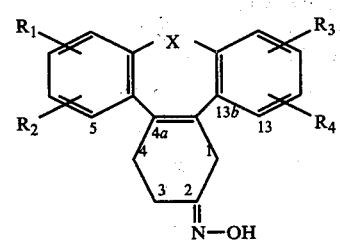

VII in which $R_1$, $R_2$, $R_3$, $R_4$ and X have the aforesaid meanings, with sodium or sodiumamalgam in a suitable liquid, such as sodium in isopropanol, or by a hydrogenation in the presence of platinumoxide (Adams catalyst) under the usual conditions, especially in acetic acid. In this reduction the $\Delta 4a(13b)$ double bond as well as the oxime moiety are reduced simultaneously.

The best method for preparation of the compounds I, in which the 4a(13b) bond is saturated, consists of a reduction of the ($\Delta 4a(13b)$) double bond of the ketone II.

A catalytic hydrogenation of the ketone II with platinum-oxide in a suitable liquid, preferably acetic acid, yields the corresponding 4a(13b)-saturated alcohol X quantitatively:

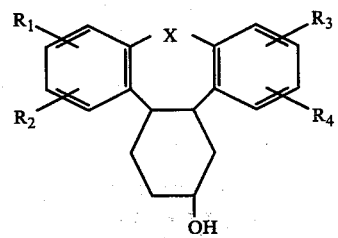

X in which $R_1$, $R_2$, $R_3$, $R_4$ and X have the meanings aforedefined. This alcohol X may be oxidized to the 4a(13b)-saturated ketone of the general formula XI:

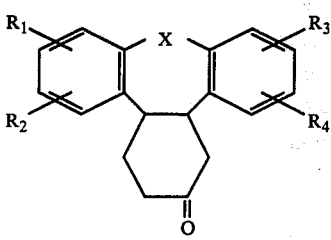

in which $R_1$, $R_2$, $R_3$, $R_4$ and X have the meanings aforedefined. This oxidation may be carried out in a conventional manner, for example with manganesedioxide or chromic acid-pyridine complex. A very useful oxidation is the biphasic one in which a benzenic solution of the alcohol X is shaken with a solution of $CrO_3$ in acetic acid/water mixture.

All additional reactions described before starting from the "unsaturated" ketone II or the corresponding alcohol, yielding the "unsaturated" compounds I can also be applied to the ketone XI or the corresponding alcohol X to obtain the 4a(13b)-saturated compounds I. In other words the ketone XI or the alcohol X can be converted into the 4a(13b)-saturated analogues of the compounds IV, VI, VII, VIII or IX followed by conversion of these compounds into the 4a(13b)-saturated compounds I in the manner described. The ketone XI can further be subjected to the reductive amination as described previously.

A specific series of biologically active intermediates used in the present methods for the preparation of the compounds I are compounds of the general formula XII:

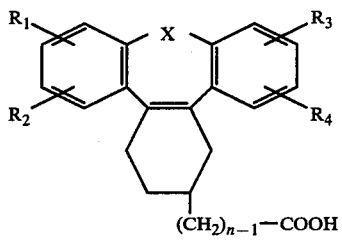

as well as salts and esters thereof, in which $R_1$, $R_2$, $R_3$, $R_4$, X and $n$ have the aforesaid meaning. These intermediates exert potent anti-inflammatory activity. They can be administered orally, parenterally or locally in a daily dose of from 0.1 mg to 10 mg per kg/body weight.

These compounds XII can be prepared in various manners, indicated already in this specification. In this connection there is referred to the hydrolysis of a cyano group and to methods such as the Wittig, Wittig-Horner and Reformatski reactions mentioned previously. In the latter methods the double bond (Δ1,2) has to be reduced additionally by means of a catalytic hydrogenation.

Compounds XII with $n = 0$ can further be prepared by treating a compound of formula IV, in which Y stands for halogen, in particular iodine, with magnesium, after which the magnesium halide thus obtained ($Y = MgHal$) is converted into the corresponding carboxyl-compound by treating with $CO_2$.

Esters of the compound XII are derived from aliphatic, cycloaliphatic, aromatic or araliphatic alcohols with 1-18 carbon atoms, which may be substituted by hydroxy or halogen groups, especially lower aliphatic alcohols with 1-6 carbon atoms, or phenylaliphatic alcohols with 7-10 C-atoms, such as methanol, ethanol, isopropanol, butanol, hexanol, phenethylalcohol, benzylalcohol, phenylpropylalcohol, p-chlorobenzylalcohol, p-hydroxyphenethylalchol, etc.

The compounds according to the invention contain an asymmetric carbon at position 2 of the tetracyclic molecule. Besides the racemate optical antipodes are thus possible which also belong to the compounds according to the invention. These optical isomers are prepared from the corresponding racemate by a resolution in the usual way. By resolving a starting product or an intermediate product in the synthesis, the optical isomers can also be obtained in a direct way.

The pharmaceutically acceptable salts of the compounds I according to the invention are acid addition salts and quaternary ammonium compounds.

The novel compounds of the formula I may be isolated from the reaction mixture in the form of a pharmaceutically acceptable acid addition salt, dependent upon the conditions in which the reaction is carried out. The acid addition salts may also be obtained by treating the free base with a pharmaceutically acceptable organic or inorganic acid. Acids that can be used in this connection are: hydrochloric acid, hydrobromic acid or hydroiodic acid, phosphoric acid, acetic acid, propionic acid, glycollic acid, maleic acid, malonic acid, succinic acid, tartaric acid, citric acid, ascorbic acid, salicyclic acid or benzoic acid.

The quaternary ammonium compounds and in particular the lower (1-4 C) alkyl quaternary ammonium compounds are obtained by reacting the compounds of the general formula I with an alkyl halide, for example methyl iodide or methyl bromide.

It is possible as a matter of course to introduce or to modify the substituents at one or both phenyl nucleii even after the condensation reactions described before. Thus a hydroxyl group can be converted into an alkoxy group, an amino group into a hydroxy- or halogen group, a methoxy group into a hydroxy group etc.

The unsubstituted or monosubstituted amines of the general formula I ($R_5$ and/or $R_6$ = H) may be alkylated in the usual way, for example by reaction with an alkyl- or aralkylhalide. More common for this purpose is, however, the acylation of the nitrogen atom in question with, for example, an acid chloride or anhydride followed by a reduction of the carbonyl group of the N-acyl derivative thus obtained. For the introduction of methyl groups at the nitrogen atom the procedure according to Eschweiler-Clarke (heating with a mixture of formaldehyd and formic acid) or the reaction with formaldehyde and sodiumcyanoborohydride in a suitable solvent, such as acetonitril, is preferred.

With an alkyl group with 1-6 carbon atoms is meant a branched or unbranced alkyl group such as methyl, ethyl, propyl, isopropyl, butyl, isobutyl, tert.butyl, n.pentyl, isopentyl and hexyl.

The alkyl group in the alkoxy and alkylthio moieties has the same meaning.

An aralkyl group mentioned in the definition of $R_5$ and $R_6$ is preferably a phenylalkyl group, in which the alkyl group contains 1-4 carbon atoms, such as benzyl, phenylethyl, phenylpropyl, phenylisopropyl, phenylbutyl and phenylisobutyl.

The heterocyclic 5- or 6-membered ring (definition of $R_5$ and $R_6$) may either be saturated or unsaturated, such as a pyrrolino group, a pyrrolidino group, a piperidino group, an oxazolidino group, a morpholino group, a piperazine group, etc.

Amines according to the general formula V, that may be used in the various condensation reactions to obtain the compounds of the invention are, for example ammonia, methylamine, dimethylamine, diethylamine, isopropylamine, dibutylamine, t.butylamine, benzylamine, phenylethylamine, phenylpropylamine, 2-phenyl-1-methyl-ethylamine, pyrroline, pyrrolidine, piperidine, oxazolidine, morpholine, piperazine, etc.

As already pointed out previously the compounds of the invention I exert a valuable central nervous system activity. This C.N.S. activity can be concluded from the results of various pharmacological experiments, such as the reserpine antagonism test, reserpine reversal test, aggression isolated mice test, ambulation test, rotarod test, grip strength test, muricidal inhibition test, etc.

The surprising high activity of the compounds I in antagonizing hypothermia induced by reserpine (reserpine antagonism test) give strong indications that the present compounds can be used as antidepressants.

The compounds I may be administered both orally and parenterally, preferably in a daily dose of from 0.1 to 10 mg per kg bodyweight.

Mixed with suitable auxiliaries the present compounds can be compressed into solid dosage units such as pills, tablets or coated tablets, or they can be processed into capsules. With the aid of suitable liquids the compounds can be applied as injection preparations in the form of solutions, emulsions or suspensions.

Preferably compounds I and, in particular, compounds I'A are used in which X stands for a methylene moiety (—CH$_2$—) or a >N-alkyl moiety, in particular a >N—CH$_3$ moiety. Especially the latter type of compounds (X = >N-alkyl) excels in a very potent antidepressant activity.

Furthermore the compounds 1, in which n is 0 or 1 are to be preferred over the compounds I, having a longer side chain (n = 2).

In the Examples the following nomenclature and numbering has been used:

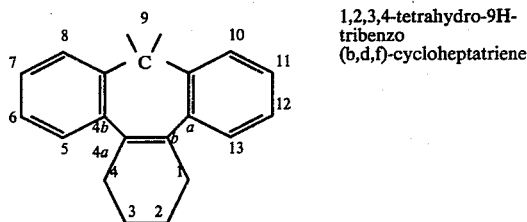

1,2,3,4-tetrahydro-9H-tribenzo(b,d,f)-cycloheptatriene

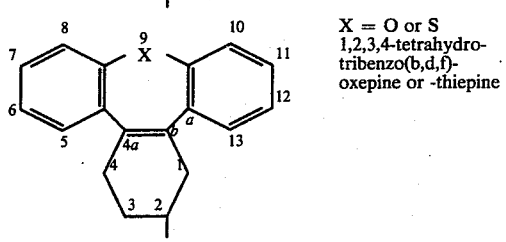

X = O or S
1,2,3,4-tetrahydro-tribenzo(b,d,f)-oxepine or -thiepine

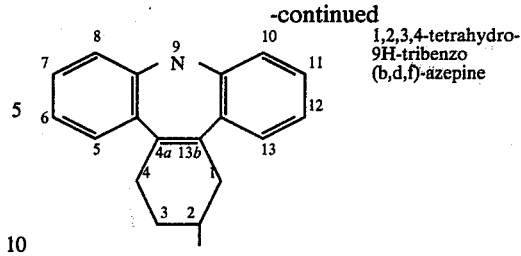

1,2,3,4-tetrahydro-9H-tribenzo(b,d,f)-azepine

By way of example the preparation of various starting products are disclosed. The preparation of analogous starting products proceeds in exactly the same way.

PREPARATION STARTING MATERIALS 1. 2-keto-1,2,3,4-tetrahydro-tribenzo(b,d,f)-oxepine To a solution of 42 g of the compound 10-keto-10,11-dihydro-dibenzo(b,f)-oxepine in 200 ml of dry ethanol a solution of sodiumethoxide (7 g of sodium in 500 ml of ethanol) is added dropwise. After stirring the mixture for 30 minutes 16.2 ml of methylvinylketon in 50 ml of ethanol are added, whereupon the solution is refluxed for 1 hour. The solution is cooled then and poured into 2 N HCl. After extracting into ether, washing the ether layer with water (till neutral) and drying the etherial phase, the solvent is evaporated.

The residue, a redcoloured oil, is chromatographed over an alumina column and used for further conversion immediately. Yield: 37% oil.

In the same manner are prepared:
2-keto-11-methyl-1,2,3,4-tetrahydro-tribenzo(b,d,f)-oxepine; melting point 146°–147° C.
2-keto-11,12-dimethyl-1,2,3,4-tetrahydro-tribenzo(b,d,f)-oxepine; (oil).
2-keto-12-chloro-1,2,3,4-tetrahydro-tribenzo(b,d,f)-oxepine; melting point 107°–108° C.
2-keto-11-trifluoromethyl-1,2,3,4-tetrahydro-tribenzo(b,d,f)-oxepine; (oil).
2-keto-6-chloro-1,2,3,4-tetrahydro-tribenzo(b,d,f)-oxepine; melting point 128°–129° C.
2-keto-6-methyl-1,2,3,4-tetrahydro-tribenzo(b,d,f)-oxepine; (oil).
2-keto-1,2,3,4-tetrahydro-tribenzo(b,d,f)-thiepine; (oil).
2-keto-1,2,3,4-tetrahydro-9H-tribenzo(b,d,f)-cycloheptatriene; melting point 132°–133° C.
2-keto-12-hydroxy-1,2,3,4-tetrahydro-9H-tribenzo(b,d,f)-cycloheptatriene; (oil).
2-keto-12-methoxy-1,2,3,4-tetrahydro-9H-tribenzo(b,d,f)-cycloheptatriene; (oil).
2-keto-11-methyl-12-methoxy-1,2,3,4-tetrahydro-9H-tribenzo(b,d,f)-cycloheptatriene; (oil).
2-keto-12-methyl-1,2,3,4-tetrahydro-9H-tribenzo(b,d,f)-cycloheptatriene; melting point 158°–163° C.
2-keto-12-trifluoromethyl-1,2,3,4-tetrahydro-9H-tribenzo(b,d,f)-cycloheptatriene; (oil).
7-keto-7-chloro-1,2,3,4-tetrahydro-9H-tribenzo(b,d,f)-cycloheptatriene; (oil).
2-keto-1,2,3,4-tetrahydro-9H-tribenzo(b,d,f)-azepine; (oil).
2-keto-9-methyl-1,2,3,4-tetrahydro-9H-tribenzo(b,d,f)-azepine; (oil).
2-keto-7-methoxy-9-methyl-1,2,3,4-tetrahydro-9H-tribenzo(b,d,f)-azepine; (oil).

2. 2-hydroxy-1,2,3,4-tetrahydro-tribenzo(b,d,f)-oxepine 6.2 g of 2-keto-1,2,3,4-tetrahydro-tribenzo(b,d,f)-oxepine are added to a suspension of 3.7 g of lithiumaluminiumhydride in 300 ml of dry ether. After refluxing for 2 hours 14.8 ml of water are added carefully. The suspension obtained is filtered off and after that the filtrate is dried and evaporated to dryness.

3. 2-hydroxy-1,2,3,4,4a,13b-hexahydro-tribenzo(b,d,f)-oxepine 1.0 g of 2-keto-1,2,3,4-tetrahydro-tribenzo(b,d,f)-oxepine is added to a suspension of 10 mg $PtO_2$ (Adams catalyst) in 50 ml glacial acetic acid. The mixture is put in a hydrogenation apparatus under hydrogen atmosphere and shaken for 3 hours. After that time the theoretical quantity of hydrogen has been absorbed. The mixture is then filtered to remove the catalyst, whereupon the filtrate is evaporated in vacuo, yielding a light yellow oil.

4. 2-mesyloxy-1,2,3,4-tetrahydro-tribenzo(b,d,f)-oxepine 6.2 g of 2-hydroxy-1,2,3,4-tetrahydro-tribenzo(b,d,f)-oxepine are added to a mixture of 16.8 ml of pyridine and methane sulphonylchloride, after which the mixture is stirred for 2 hours at 0° C. and then another 2 hours at room temperature. After that the mixture is poured out into water and then extracted with ether. The ether layers are dried and evaporated to dryness.

5. 2-azido-1,2,3,4-tetrahydro-tribenzo(b,d,f)-oxepine

The mesylate obtained in 3 in brought into a mixture of 25 ml of dimethylformamide and 4.2 ml of water, to which 1.52 g of activated sodium azide is added. The mixture is refluxed for 5 hours. After cooling the mixture is poured out into water and extracted with ether. After that the ether layers are washed dried, and evaporated to dryness.

6. 2-cyano-1,2,3,4-tetrahydro-tribenzo(b,d,f)-oxepine 2.62 g of the 2-hydroxy compound obtained in 2 is dissolved in 50 ml of benzene whereupon 5 g of phosphorus triiodide is added. The mixture is refluxed for 2 hours. After cooling this mixture ice-water is cautiously added. The organic layer is separated, washed with water and dried. The solvent (benzene) is then evaporated yielding 3.6 g of the oily 2-iodo-compound. This residue is immediately dissolved in 300 ml dimethylformamide, after which 4 g sodiumcyanide is added. The mixture obtained is heated at 90° C. for 1 hour stirring all the time. The reaction-mixture is then poured into 600 ml water and extracted with ether. The crude nitrile is obtained after evaporation of the ether and immediately used for further reactions.

7. 2-cyanomethylidene-1,2,3,4-tetrahydro-tribenzo(b,d,f)-oxepine 1 g of 2-keto-1,2,3,4-tetrahydro-tribenzo(b,d,f)-oxepine is mixed with 1 ml of benzene, 15 ml of acetonitrile and 0.5 g of molecular sieve (4 Å). 50 mg of sodium-ethoxide are added and the mixture is heated for 3 hours (90°-100° C.). After cooling the mixture the molecular sieve is filtered off and the filtrate evaporated.

EXAMPLE I 2-amino-1,2,3,4-tetrahydro-tribenzo(b,d,f)-oxepine 3.7 g of 2-azido-1,2,3,4-tetrahydro-tribenzo(b,d,f)-oxepine are added to a suspension of 3 g of lithiumaluminiumhydride in 100 ml of dry ether. The mixture is refluxed for 1 hour. After the mixture has been cooled down, 12 ml of water are added carefully after which the mixture is stirred for some time. The suspension is filtered and after that the filtrate is dried and evaporated to dryness. The residue is converted with maleic acid into the maleate. Melting point of the maleate: 198°-202° C. Yield 85%.

EXAMPLE II

In the way indicated in example I are prepared:
2-amino-9-methyl-1,2,3,4-tetrahydro-9H-tribenzo(b,d,f)-azepine, (oil).
2-amino-7-chloro-9-methyl-1,2,3,4-tetrahydro-9H-tribenzo(b,d,f)-azepine, (oil).
2-amino-1,2,3,4-tetrahydro-9H-tribenzo(b,d,f)-cycloheptatriene; melting point as maleate: 185°-188° C.
2-amino-12-methoxy-1,2,3,4-tetrahydro-9H-tribenzo(b,d,f)-cycloheptatriene; melting point as maleate: 165° C. (dec.).
2-amino-12-methyl-1,2,3,4-tetrahydro-9H-tribenzo(b,d,f)-cycloheptatriene; melting point as maleate: 196°-201° C.
2-amino-7-chloro-1,2,3,4-tetrahydro-9H-tribenzo(b,d,f)-cycloheptatriene, (oil).
2-amino-11-trifluoromethyl-1,2,3,4-tetrahydro-tribenzo(b,d,f)-oxepine, (oil).
2-amino-11-methyl-1,2,3,4-tetrahydro-tribenzo(b,d,f)-oxepine; melting point as maleate: 190°-192° C.
2-amino-12-chloro-1,2,3,4-tetrahydro-tribenzo(b,d,f)-oxepine; melting point as maleate: 194°-196° C.
2-amino-1,2,3,4-tetrahydro-tribenzo(b,d,f)-thiepine; melting pont as maleate: 178°-180° C.
2-amino-12-trifluoromethyl-1,2,3,4-tetrahydro-9H-tribenzo(b,d,f)-cycloheptatriene, (oil).
2-amino-12-hydroxy-1,2,3,4-tetrahydro-9H-tribenzo(b,d,f)-cycloheptatriene, (oil).

EXAMPLE III 2-dimethylamino-1,2,3,4-tetrahydro-9H-tribenzo(b,d,f)-cycloheptatriene In a 500 ml Parr apparatus a mixture of 20 g 2-keto-1,2,3,4-tetrahydro-tribenzo(b,d,f)-cycloheptatriene in 300 ml of absolute ethanol and a solution of 6 g of dimethylamine in 20 ml of ethanol to which 3.9 g of palladium 10% on charcoal are added, is hydrogenated by means of hydrogen under a pressure of 3 kg/cm².

The mixture is then filtered and the filtrate washed, dried and evaporated to dryness. The residue is an oily substance. The oil is crystallized by means of maleic acid. Melting point after recrystallization from ether-ethanol 145°-150° C. and 169°-171° C. (double melting point).

Treatment of the free base with methyliodide resulted in the iodo methylate.

EXAMPLE IV 2-dimethylamino-6-chloro-1,2,3,4-tetrahydro-tribenzo(b,d,f) oxepine To a mixture of 10 ml of dimethylamine and 3.1 ml of 98% formic acid at −10° C. a solution of 11.5 g of 2-keto-6-chloro-1,2,3,4-tetrahydro-tribenzo(b,d,f)-oxepine in 30 ml of dimethylformamide are added dropwise. The mixture is refluxed for 10 hours. After cooling, the mixture is poured into water and extracted into ether. The ether layer is then washed with 300 ml of 2 N HCl. The acidic water layer is made alkaline with 2 N NaOH, after which the alkaline aqueous solution is extracted with ether once more. The ether layers are collected, dried and then evaporated. The oil obtained crystallizes as maleate: melting point 171° C.

EXAMPLE V 2-dimethylamino-12-methoxy-1,2,3,4-tetrahydro-9H-tribenzo(b,d,f)-cycloheptatriene 500 mg of 2-keto-12-methoxy-1,2,3,4-tetrahydro-9H-tribenzo(b,d,f)-cycloheptatriene in 2.7 ml of methanol is treated with 150 ml of sodiumborohydride and 0.14 ml of methanolic HCl solution (5 N). After mixing for 10 hours at an elevated temperature, the reaction mixture is filtered and the filtrate extracted with ether. The ether layer is washed, dried and evaporated. The oil obtained is then chromatographed over an alumina column. Melting point as HCl salt: 210° C. Yield 30%.

EXAMPLE VI

In the way indicated in example III are prepared:
2-dimethylamino-7-methoxy-9-methyl-1,2,3,4-tetrahydro-9H-tribenzo(b,d,f)-azepine, (oil).
2-amino-1,2,3,4-tetrahydro-9H-tribenzo(b,d,f)-cycloheptatriene; melting point as maleate: 183°-185° C.
2-methylamino-1,2,3,4-tetrahydro-9H-tribenzo(b,d,f)-cycloheptatriene; melting point as maleate: 162°-165° C.
2-dimethylamino-12-methoxy-1,2,3,4-tetrahydro-9H-tribenzo(b,d,f)-cycloheptatriene; melting point HCl salt: 210° C. (dec.).
2-dimethylamino-12-chloro-1,2,3,4-tetrahydro-tribenzo(b,d,f)-oxepine; melting point maleate: 195°-196° C.
2-dimethylamino-1,2,3,4-tetrahydro-tribenzo(b,d,f)-thiepine; melting point HCl salt: 250°-255° C. (dec.).
2-morpholino-1,2,3,4-tetrahydro-tribenzo(b,d,f)-thiepine, (oil).
2-dimethylamino-9-methyl-1,2,3,4-tetrahydro-9H-tribenzo(b,d,f)-azepine, (oil); maleate salt 212°-218° C.
2-methylamino-9-methyl-1,2,3,4-tetrahydro-9H-tribenzo(b,d,f)-azepine, (oil).
2-piperidino-9-methyl-1,2,3,4-tetrahydro-9H-tribenzo(b,d,f)-azepine, (oil).
2-benzylamino-9-methyl-1,2,3,4-tetrahydro-9H-tribenzo(b,d,f)-azepine, (oil).
2-benzylamino-1,2,3,4-tetrahydro-9H-tribenzo(b,d,f)-cycloheptatriene, (oil).
2-phenethylamino-1,2,3,4-tetrahydro-9H-tribenzo(b,d,f)-cycloheptatriene, (oil).
2-amino-1,2,3,4-tetrahydro-tribenzo(b,d,f)-thiazepine, (oil); melting point maleate: 178° C.
2-dimethylamino-1,2,3,4-tetrahydro-tribenzo(b,d,f)-thiazepine, (oil); melting point HCl salt: 250° C. (dec.).
2-dimethylamino-7-hydroxy-9-methyl-1,2,3,4-tetrahydro-9H-tribenzo(b,d,f)-azepine, (oil).
2-dimethylamino-9,12-dimethyl-1,2,3,4-tetrahydro-9H-tribenzo(b,d,f)-azepine, (oil).
2-dimethylamino-9-methyl-11-trifluoromethyl-1,2,3,4-tetrahydro-9H-tribenzo(b,d,f)-azepine, (oil).

EXAMPLE VII

In the way indicated in example IV are prepared:
2-dimethylamino-1,2,3,4-tetrahydro-9H-tribenzo(b,d,f)-cycloheptatriene; melting point maleate: 145°-150° C. and 169°-171° C.
2-dimethylamino-12-methoxy-1,2,3,4-tetrahydro-9H-tribenzo(b,d,f)-cycloheptatriene; m.p. HCl salt: 210° C.
2-dimethylamino-12-methyl-1,2,3,4-tetrahydro-9H-tribenzo(b,d,f)-cycloheptatriene; m.p. maleate: 198°-201° C.
2-dimethylamino-7-chloro-1,2,3,4-tetrahydro-9H-tribenzo(b,d,f)-cycloheptatriene, (oil).
2-dimethylamino-1,2,3,4-tetrahydro-tribenzo(b,d,f)-oxepine; melting point maleate: 103°-108° C.
2-dimethylamino-11-methyl-1,2,3,4-tetrahydro-tribenzo(b,d,f)-oxepine; melting point maleate: 140°-142° C.
2-dimethylamino-11,12-dimethyl-1,2,3,4-tetrahydro-tribenzo(b,d,f)-oxepine, (oil).
2-dimethylamino-12-chloro-1,2,3,4-tetrahydro-tribenzo(b,d,f)-oxepine; melting point maleate: 195°-196° C.
2-dimethylamino-6-methyl-1,2,3,4-tetrahydro-tribenzo(b,d,f)-oxepine; melting point maleate: 182°-183° C.
2-dimethylamino-11-methyl-12-methoxy-1,2,3,4-tetrahydro-9H-tribenzo(b,d,f)-cycloheptatriene, (oil).
2-morpholino-1,2,3,4-tetrahydro-9H-tribenzo(b,d,f)-cycloheptatriene, (oil).
2-piperidino-9-methyl-1,2,3,4-tetrahydro-9H-tribenzo(b,d,f)-azepine, (oil).
2-dimethylamino-1,2,3,4-tetrahydro-tribenzo(b,d,f)-thiepine; melting point HCl salt: 250°-255° C.
2-dimethylamino-9-methyl-1,2,3,4-tetrahydro-9H-tribenzo(b,d,f)-azepine; melting point maleate: 210°-220° C. (dec.).
2-dimethylamino-11-trifluoromethyl-1,2,3,4-tetrahydro-tribenzo(b,d,f)-oxepine, (oil).
2-dimethylamino-1,2,3,4-tetrahydro-9H-tribenzo(b,d,f)-azepine, (oil).

EXAMPLE VIII

In the way indicated in example V, the following compounds are prepared:
2-amino-1,2,3,4-tetrahydro-tribenzo(b,d,f)-oxepine; melting point maleate: 198°-200° C.
2-methylamino-1,2,3,4-tetrahydro-tribenzo(b,d,f)-oxepine, (oil).
2-morpholino-1,2,3,4-tetrahydro-tribenzo(b,d,f)-oxepine, (oil).
2-dimethylamino-1,2,3,4-tetrahydro-tribenzo(b,d,f)-oxepine; melting point maleate: 105°-110° C.
2-dimethylamino-1,2,3,4-tetrahydro-9H-tribenzo(b,d,f)-cycloheptatriene; melting point maleate: 145°-150° C. (and 168°-170° C.).

2-dimethylamino-12-methyl-1,2,3,4-tetrahydro-9H-tribenzo(b,d,f)-cycloheptatriene; melting point maleate: 198°–200° C.
2-dimethylamino-12-hydroxy-1,2,3,4-tetrahydro-9H-tribenzo(b,d,f)-cycloheptatriene, (oil).
2-dimethylamino-11-methyl-1,2,3,4-tetrahydro-tribenzo(b,d,f)-oxepine; melting point maleate: 138°–142° C.
2-amino-11-methyl-1,2,3,4-tetrahydro-tribenzo(b,d,f)-oxepine; melting point maleate: 190°–193° C.
2-pyrrolidino-1,2,3,4-tetrahydro-9H-tribenzo(b,d,f)-cycloheptatriene, (oil).
2-diethylamino-12-methyl-1,2,3,4-tetrahydro-9H-tribenzo(b,d,f)-cycloheptatriene; melting point maleate: 187°–192° C.
2-amino-1,2,3,4-tetrahydro-tribenzo(b,d,f)-thiepine; melting point maleate: 178°–180° C.
2-dimethylamino-1,2,3,4-tetrahydro-tribenzo(b,d,f)-thiepine; melting point HCl salt: 250° C. (dec.).
2-dimethylamino-9-methyl-1,2,3,4-tetrahydro-9H-tribenzo(b,d,f)-azepine; melting point maleate: 210°–228° C. (dec.).
2-dimethylamino-12-trifluoromethyl-1,2,3,4-tetrahydro-9H-tribenzo(b,d,f)-cycloheptatriene, (oil).

EXAMPLE IX 2-dimethylamino-1,2,3,4-tetrahydro-tribenzo(b,d,f)-oxepine 1.7 g of 2-amino-1,2,3,4-tetrahydro-tribenzo(b,d,f)-oxepine is dissolved in 47.2 ml of formic acid and 47.2 ml of a 40% solution of formaldehyde in water. The mixture is heated at 100° C. for 5 hours after which the mixture is cooled. The solution is then poured into water and made alkaline with diluted sodiumhydroxide. After that the mixture is extracted with ether and the ether layers obtained dried and evaporated. The oil obtained crystallizes with maleic acid as maleate: melting point 103°–108° C. Obtained in this manner: 53%.

EXAMPLE X 2-dimethylamino-12-methoxy-1,2,3,4-tetrahydro-9H-tribenzo(b,d,f)-cycloheptatriene To a solution of 1 g of 2-amino-12-methoxy-1,2,3,4-tetrahydro-9H-tribenzo-cycloheptatriene in 15 ml of acetonitril, 2.7 ml of a 40% formaldehyde solution in water and 660 mg of cyanoborohydride are added. The reaction is exothermic. After stirring for 1 hour 0.8 ml of acetic acid is added after which the mixture is stirred for another 2 hours. The solution is made alkaline after that and then extracted with ether. The ether layer is dried and evaporated. Melting point HCl salt: 210° C.

EXAMPLE XI 2-dimethylaminoethyl-1,2,3,4-tetrahydro-9H-tribenzo(b,d,f)-cycloheptatriene 22.50 g of triethylphosphonoacetate (prepared by means of the Michaelis-Arbuzow reaction) is added dropwise at 20° C. to a slurry of 50% sodium hydride (4.9 g) in 200 ml of dry 1,2-dimethoxy-ethane. After addition the reaction mixture is stirred for 1 hour at room temperature until gas evolution ceased. Then 26 g of 2-keto-1,2,3,4-tetrahydro-9H-tribenzo(b,d,f)-cycloheptatriene is added slowly at such a rate that the temperature is maintained below 40° C. After an additional quarter of an hour the mixture is poured into a large excess of water and the aqueous solution extracted with ether. The ether layer after being dried over sodiumsulphate and evaporated gives 26.0 g of 2-ethoxycarbonylmethyl-3,4-dihydro-9H-tribenzo(b,d,f)-cycloheptatriene.

Catalytic hydrogenation of 15 g of this product in methanol and palladium/charcoal-catalyst gives the 1,2,3,4-tetrahydro-compound. After evaporation of the methanol to a volume of 70 ml, the mixture is treated with 30 g of dimethylamine in an ampoule at 100° C. for 14 hours to give the 2-dimethylamino-carbonylmethyl-compound, 13.5 g. This product is reduced with 15 g lithiumaluminiumhydride in ether (8 hours at boiling temperature) in the usual manner yielding 13.0 g of the title compound. The oily residue is converted to the maleate, melting point 131°–133° C.

The same product is obtained by carrying out the hydrogenation with palladium on charcoal in the last step of the synthesis instead of performing this hydrogenation previous to the amide formation and subsequent reduction of the amide moiety with LiAlH$_4$.

In the same manner are prepared:
2-dimethylaminoethyl-9-methyl-1,2,3,4-tetrahydro-9H-tribenzo(b,d,f)-azepine and
2-aminoethyl-1,2,3,4-tetrahydro-tribenzo(b,d,f)-oxepine.

EXAMPLE XII 2-aminomethyl-1,2,3,4-tetrahydro-9H-tribenzo(b,d,f)-cycloheptatriene 1.4 g of the 2-cyano-compound, prepared in a similar manner as described (see "starting materials" 6) is dissolved in 50 ml tetrahydrofuran after which 1.5 g LiAlH$_4$ is added. The mixture is boiled for 4 hours. After cooling 12 ml of water is added slowly while stirring. Filtration and evaporation of the solvent yields 2.4 g of the 2-aminomethyl-compound as an oil. Melting point maleate salt: 125°–132° C.

In the same manner are prepared:
2-aminomethyl-1,2,3,4-tetrahydro-tribenzo(b,d,f)-oxepine.
2-aminomethyl-9-methyl-1,2,3,4-tetrahydro-9H-tribenzo(b,d,f)-azepine.
2-aminomethyl-7-methoxy-10-chloro-1,2,3,4-tetrahydro-9H-tribenzo(b,d,f)-cycloheptatriene.

EXAMPLE XIII 2-dimethylaminomethyl-1,2,3,4-tetrahydro-tribenzo(b,d,f)-oxepine 1.5 g of 2-cyano-1,2,3,4-tetrahydro-tribenzo(b,d,f)-oxepine ("starting material 6") is suspended in 80 ml diethyleneglycol and 65 ml of an aqueous KOH solution (40%). The mixture is refluxed for 5 hours. After cooling the mixture to ambient temperature, it is poured into 450 ml water. The aqueous mixture is extracted with ether to remove non-acidic material. The water-phase is acidified to about pH 3, whereupon the mixture is extracted with ether. The ether extracts are washed, dried and then evaporated, yielding 0.80 g of the crude 2-carboxy-1,2,3,4-tetrahydro-tribenzo(b,d,f)-oxepine. This carboxyl-compound is converted into the dimethylamide in the usual manner and then reduced with LiAlH$_4$, yielding 0.5 g of the title product as an oil.

In the same manner are prepared:
2-dimethylaminomethyl-9-methyl-1,2,3,4-tetrahydro-9H-tribenzo(b,d,f)-azepine, (oil).
2-dimethylaminomethyl-1,2,3,4-tetrahydro-9H-tribenzo(b,d,f)-cycloheptatriene, (oil).

2-aminomethyl-1,2,3,4-tetrahydro-9H-tribenzo(b,d,f)-cycloheptatriene, (oil).

2-benzylaminomethyl-9-methyl-1,2,3,4-tetrahydro-9H-tribenzo(b,d,f)-azepine, (oil).

EXAMPLE XIV 2-aminoethyl-1,2,3,4-tetrahydro-9H-tribenzo(b,d,f)-cycloheptatriene Diborane gas, obtained from 1.2 g of $NaBH_4$ and 5.2 ml of $BF_3$-etherate is let in into a solution of 200 mg of 2-cyanomethylidene-1,2,3,4-tetrahydro-9H-tribenzo(b,d,f)-cycloheptatriene (obtained in a similar manner as described in "Starting materials" 7) in 15 ml THF under nitrogen atmosphere.

After that the mixture is refluxed for 1 hour. The excess of $B_2H_5$ present is then decomposed by adding ethanol, whereupon the solution is evaporated.

The residue is dissolved in 18 ml of a mixture of concentrated HCl and water (1:1) whereupon the solution is heated for some time. The acidic water layer is cooled down, made alkaline and then extracted into ether. Evaporating the solvent yields 85 mg of the title compound as an oil.

In the same manner as prepared:
2-aminomethyl-1,2,3,4-tetrahydro-tribenzo(b,d,f)-oxepine.
2-aminomethyl-1,2,3,4-tetrahydro-9H-tribenzo(b,d,f)-azepine.

EXAMPLE XV 2-amino-1,2,3,4,4a,13b-hexahydro-9H-tribenzo(b,d,f)-cycloheptatriene 10 g of 2-keto-1,2,3,4-tetrahydro-9H-tribenzo(b,d,f)-cycloheptatriene is suspended in 400 ml of ethanol and subsequently 20 g hydroxylamine.HCl and 40 ml pyridine are added. After refluxing the mixture for 30 minutes, the mixture is concentrated to a thin oil in vacuo, from which the oxime crystallized slowly. The precipitate is sucked off and washed with water. The dried oxime is suspended in isopropanol. Over a period of 3 hours 20 g sodium are added while stirring. The reaction mixture is concentrated to one-fourth of its volume by evaporation (Rotavap) and then diluted with water and extracted with ether. The ether extract was dried over anhydrous potassium carbonate and finally evaporated to dryness. The oil obtained is converted into its maleate, melting point 212°–213° C. Yield 7.3 g.

In the same way are prepared:
2-amino-1,2,3,4,4a,13b-hexahydro-tribenzo(b,d,f)-oxepine and
2-amino-9-methyl-1,2,3,4,4a,13b-hexahydro-9H-tribenzo(b,d,f)-azepine.

By using palladium on charcoal (10%) the oxime is hydrogenated into the 4a,13b-unsaturated compound: 2-amino-1,2,3,4-tetrahydro-9H-tribenzo(b,d,f)-cycloheptatriene, (oil); melting point maleate: 181°–186° C.

EXAMPLE XVI 2-dimethylamino-1,2,3,4,4a,13b-hexahydro-9H-tribenzo(b,d,f)-cycloheptatriene 4 g of the primary amine prepared according to example XV is methylated with a formaldehyde/formic acid mixture (1:1) during 5 hours at 100° C., (Clarke-Eschweiler procedure). Obtained is 4.2 g of the dimethylamino product which is converted to its hydrochloride, melting point 256°–263° C.

EXAMPLE XVII 2-dimethylamino-1,2,3,4,4a,13b-hexahydro-9H-tribenzo(b,d,f)-cycloheptatriene In the same manner as described in Example IV the compound 2-keto-1,2,3,4,4a,13b-hexahydro-9H-tribenzo(b,d,f)-cycloheptatriene, obtained by oxydation of the corresponding alcohol with chromic acid in benzene, acetic acid, water at room temperature, is reacted with dimethylamine and formic acid in dimethylformamide at reflux temperature. Melting point HCl salt 260°–263° C.

The same product is obtained by converting 2-hydroxy-1,2,3,4,4a,13b-hexahydro-9H-tribenzo(b,d,f)-cycloheptatriene, obtained by hydrogenating the corresponding 2-keto-1,2,3,4-tetrahydro-compound with $PtO_2$ in glacial acetic acid, into 2-mesyloxy-1,2,3,4,4a,13b-hexahydro-9H-tribenzo(b,d,f)-cycloheptatriene in the same manner as described in "starting materials" 3 and 4 and treating this mesyloxy compound with dimethylamine.

In the same manners are prepared:
2-dimethylamino-1,2,3,4,4a,13b-hexahydro-tribenzo(b,d,f)-oxepine.
2-dimethylamino-9-methyl-1,2,3,4,4a,13b-hexahydro-9H-tribenzo(b,d,f)-azepine.
2-dimethylamino-1,2,3,4,4a,13b-hexahydro-tribenzo(b,d,f)-thiazepine.
2-dimethylamino-12-methyl-1,2,3,4,4a,13b-hexahydro-9H-tribenzo(b,d,f)-cycloheptatriene.
2-methylamino-1,2,3,4,4a,13b-hexahydro-tribenzo(b,d,f)-oxepine.
2-dimethylamino-7-methoxy-9-methyl-1,2,3,4,4a,13b-hexahydro-9H-tribenzo(b,d,f)-azepine.
2-morpholino-9-methyl-1,2,3,4,4a,13b-hexahydro-9H-tribenzo(b,d,f)-azepine.

EXAMPLE XVIII 2-carboxy-1,2,3,4-tetrahydro-9H-tribenzo(b,d,f)-cycloheptatriene In the manner described in example XIII 2.3 g 2-cyano-1,2,3,4-tetrahydro-9H-tribenzo(b,d,f)-cycloheptatriene is hydrolysed into the corresponding 2-carboxy-compound. Recrystallization from benzene gives 1.2 g of the pure carboxy-compound; meiting point 196°–202° C., which is then converted into the methyl-, butyl-, benzyl- and phenethylester.

In the same way are prepared:
2-carboxy-7-methoxy-1,2,3,4-tetrahydro-9H-tribenzo(b,d,f)-cycloheptatriene.
2-carboxy-7-methoxy-10-chloro-1,2,3,4-tetrahydro-9H-tribenzo(b,d,f)-cycloheptatriene.
2-carboxy-9-methyl-1,2,3,4-tetrahydro-9H-tribenzo(b,d,f)-azepine and the corresponding 7-methoxy compound.
2-carboxy-1,2,3,4-tetrahydro-tribenzo(b,d,f)-thiazepine.
2-carboxy-12-methyl-1,2,3,4-tetrahydro-9H-tribenzo(b,d,f)-cycloheptatriene.

EXAMPLE XIX 2-carboxymethyl-1,2,3,4-tetrahydro-9H-tribenzo(b,d,f)-cycloheptatriene 10 g of the ethoxycarbonylmethyl-compound obtained in the example XI is heated in a mixture of 15 g of potassium hydroxide, 10 ml of water and 200 ml of ethanol for 2 hours at boiling temperature. The mixture is concentrated in vacuo to about 50 ml, diluted with water and acidified to pH 3 with hydrochloric acid. Extraction with benzene and evaporation of the solvent gives 9.5 g of the title compound.

In the same manner is prepared:
2-carboxymethyl-9-methyl-1,2,3,4-tetrahydro-9H-tribenzo(b,d,f)-cycloheptatriene.

EXAMPLE XX 2-aminomethyl-1,2,3,4,4a,13b-hexahydro-9H-tribenzo(b,d,f)-cycloheptatriene 2-hydroxy-1,2,3,4,4a,13b-hexahydro-9H-tribenzo(b,d,f)-cycloheptatriene is converted into the corresponding 2-mesyloxy compound in the same manner as described in "starting materials" 4 and then treated with sodiumcyanide, to obtain the 2-cyano-compound. This compound is immediately reduced with LiAlH$_4$ in ether as described previously, yielding the 2-aminomethyl-compound as an oil.

Conversion of this oil with maleic acid yields the maleate; melting point: 128°–132° C.

In the same manner is prepared:
2-aminomethyl-9-methyl-1,2,3,4,4a,13b-hexahydro-9H-tribenzo(b,d,f)-azepine.

I claim:

1. A compound of the formula:

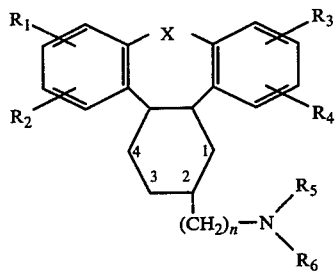

I or a pharmaceutically acceptable salt thereof, in which
X represents the group consisting of oxygen and sulphur,
$R_1$, $R_2$, $R_3$ and $R_4$ are selected from the group consisting of hydrogen, hydroxy, halogen, alkyl having 1 to 6 carbon atoms, alkoxy having 1 to 6 carbon atoms, alkylthio having 1 to 6 carbon atoms and trifluoromethyl,
$R_5$, $R_6$ are selected from the group consisting of hydrogen, alkyl having 1 to 6 carbon atoms, aralkyl having 7 to 10 carbon atoms, and together in combination with the nitrogen atom a morpholine ring,
n is selected from 0, 1 and 2, and
the dotted line signifies an optional bond.

2. A compound according to claim 1 of the formula I A:

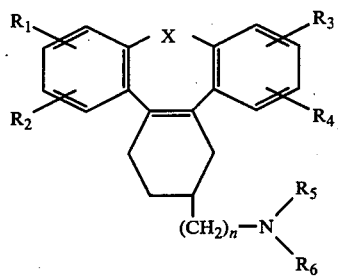

1 A in which $R_1$, $R_2$, $R_3$, $R_4$, $R_5$, $R_6$, X and n have the meanings indicated in claim 1.

3. A compound of the formula I according to claim 1 in which n is the number 0 or 1.

4. The compound of claim 1 wherein $R_6$ is selected from the group consisting of hydrogen and alkyl having 1 to 6 carbon atoms.

5. The compound of claim 1 which is 2-dimethylamino-1,2,3,4-tetrahydro-tribenzo-(b,d,f)-oxepine.

6. The compound of claim 1 which is 2-amino-1,2,3,4-tetrahydro-tribenzo(b,d,f)-oxepine.

7. The compound of claim 1 which is 2-amino-11-trifluoromethyl-1,2,3,4-tetrahydro-tribenzo(b,d,f)-oxepine.

8. The compound of claim 1 which is 2-amino-11-methyl-1,2,3,4-tetrahydro-tribenzo(b,d,f)-oxepine.

9. The compound of claim 1 which is 2-amino-12-chloro-1,2,3,4-tetrahydro-tribenzo(b,d,f)-oxepine.

10. The compound of claim 1 which is 2-dimethylamino-6-chloro-1,2,3,4-tetrahydro-tribenzo(b,d,f)-oxepine.

11. The compound of claim 1 which is 2-dimethylamino-12-chloro-1,2,3,4-tetrahydro-tribenzo(b,d,f)-oxepine.

12. The compound of claim 1 which is 2-dimethylamino-11-methyl-1,2,3,4-tetrahydro-tribenzo(b,d,f)-oxepine.

13. The compound of claim 1 which is 2-dimethylamino-11,12-dimethyl-1,2,3,4-tetrahydro-tribenzo(b,d,f)-oxepine.

14. The compound of claim 1 which is 2-dimethylamino-6-methyl-1,2,3,4-tetrahydro-tribenzo(b,d,f)-oxepine.

15. The compound of claim 1 which is 2-dimethylamino-11-trifluoromethyl-1,2,3,4-tetrahydro-tribenzo(b,d,f)-oxepine.

16. The compound of claim 1 which is 2-methylamino-1,2,3,4-tetrahydro-tribenzo(b,d,f)-oxepine.

17. The compound of claim 1 which is 2-dimethylamino-1,2,3,4-tetrahydro-tribenzo(b,d,f)-oxepine.

18. The compound of claim 1 which is 2-aminoethyl-1,2,3,4-tetrahydro-tribenzo(b,d,f)-oxepine.

19. The compound of claim 1 which is 2-aminomethyl-1,2,3,4-tetrahydro-tribenzo(b,d,f)-oxepine.

20. The compound of claim 1 which is 2-dimethylaminomethyl-1,2,3,4-tetrahydro-tribenzo(b,d,f)-oxepine.

21. The compound of claim 1 which is 2-amino-1,2,3,4,4a,13b-hexahydro-tribenzo(b,d,f)-oxepine.

22. The compound of claim 1 which is 2-dimethylamino-1,2,3,4a,13b-hexahydro-tribenzo(b,d,f)-oxepine.

23. The compound of claim 1 which is 2-methylamino-1,2,3,4,4a,13b-hexahydro-tribenzo(b,d,f)-oxepine.

24. The compound of claim 1 which is 2-amino-1,2,3,4-tetrahydro-tribenzo(b,d,f)-thiepine.

25. The compound of claim 1 which is 2-dimethylamino-1,2,3,4-tetrahydro-tribenzo(b,d,f)-thiepine.

26. The compound of claim 1 which is 2-morpholino-1,2,3,4-tetrahydro-tribenzo(b,d,f)-oxepine.

27. The compound of claim 1 which is 2-morpholino-1,2,3,4-tetrahydro-tribenzo(b,d,f)-thiepine.

* * * * *